United States Patent
Kong et al.

(10) Patent No.: US 7,414,017 B2
(45) Date of Patent: *Aug. 19, 2008

(54) LOW RESIDUE CLEANING SOLUTION COMPRISING A C8-C10 ALKYLPOLYGLUCOSIDE

(75) Inventors: Stephen Bradford Kong, Alamo, CA (US); Sonia H. Burciaga, Tracy, CA (US); Andrew Kilkenny, Livermore, CA (US)

(73) Assignee: The Clorox Company, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/780,056

(22) Filed: Jul. 19, 2007

(65) Prior Publication Data

US 2008/0010772 A1 Jan. 17, 2008

Related U.S. Application Data

(63) Continuation-in-part of application No. 11/612,672, filed on Dec. 19, 2006, now Pat. No. 7,345,015, and a continuation-in-part of application No. 09/939,383, filed on Aug. 24, 2001, now abandoned, and a continuation-in-part of application No. 09/939,179, filed on Aug. 24, 2001, now abandoned, which is a continuation-in-part of application No. 09/737,641, filed on Dec. 14, 2000, now abandoned.

(51) Int. Cl.
*C11D 3/22* (2006.01)
*C11D 3/48* (2006.01)
*C11D 3/44* (2006.01)

(52) U.S. Cl. .......... 510/295; 510/238; 510/362; 510/382; 510/384; 510/438; 510/391; 510/432; 510/470

(58) Field of Classification Search .......... 510/295, 510/238, 362, 382, 384, 391, 432, 438, 470
See application file for complete search history.

(56) References Cited

U.S. PATENT DOCUMENTS

| | | | |
|---|---|---|---|
| 4,753,844 A | 6/1988 | Jones et al. | |
| 5,342,534 A | 8/1994 | Skrobala et al. | |
| 5,576,284 A | 11/1996 | Van Buskirk et al. | |
| 6,159,924 A | 12/2000 | Weller et al. | |
| 6,384,010 B1 | 5/2002 | Wagers | |
| 6,489,285 B2 | 12/2002 | Faber | |
| 6,642,197 B1 | 11/2003 | Cheung et al. | |
| 6,716,805 B1 | 4/2004 | Sherry et al. | |
| 6,743,819 B1 | 6/2004 | Manzer | |
| 6,786,223 B2 | 9/2004 | Klinkhammer et al. | |
| 6,814,088 B2 | 11/2004 | Barnabas et al. | |
| 6,841,527 B2 | 1/2005 | Mitra et al. | |
| 6,849,589 B2 | 2/2005 | Liu | |
| 6,936,580 B2 | 8/2005 | Sherry et al. | |
| 7,048,806 B2 * | 5/2006 | Ochomogo et al. | 134/34 |
| 7,082,951 B2 | 8/2006 | Barnabas et al. | |
| 7,094,741 B2 | 8/2006 | Barnabas et al. | |
| 2003/0100465 A1 * | 5/2003 | Kilkenny et al. | 510/384 |
| 2003/0216281 A1 * | 11/2003 | DeLeo et al. | 510/475 |
| 2005/0121054 A1 | 6/2005 | Barnabas et al. | |

* cited by examiner

*Primary Examiner*—Charles I Boyer
(74) *Attorney, Agent, or Firm*—David Peterson

(57) ABSTRACT

Cleaning compositions containing C8-C10 alkylpolyglucosides, have low filming and streaking when combined with C2-C4 alcohols and propylene glycol ethers. The low filming and streaking occurs even in the presence of quaternary ammonium biocides.

22 Claims, No Drawings

LOW RESIDUE CLEANING SOLUTION COMPRISING A C8-C10 ALKYLPOLYGLUCOSIDE

The present invention is a continuation-in-part of U.S. patent application Ser. No. 11/612,672 filed Dec. 19, 2006 now U.S. Pat. No. 7,345,015 entitled "Low Residue Cleaning Solution for Disinfecting Wipes," and is incorporated herein by reference. The present invention is a also continuation-in-part of U.S. patent application Ser. No. 09/939,383 filed Aug. 24, 2001 now abandoned entitled "Bactericidal Cleaning Wipe," and is incorporated herein by reference. The present invention is also a continuation-in-part of U.S. patent application Ser. No. 09/939,179 filed Aug. 24, 2001 now abandoned entitled "Bactericidal Cleaning Wipe," which in turn is a continuation-in-part of U.S. patent application Ser. No. 09/737,641 filed Dec. 14, 2000 now abandoned entitled "Bactericidal Cleaning Wipe." U.S. patent application Ser. Nos. 09/939,179 filed Aug. 24, 2001 and 09/737,641 filed Dec. 14, 2000 are incorporated herein by reference.

BACKGROUND OF THE INVENTION

1. Field of the Invention

The present invention relates generally to a composition and method for reducing residue left by wet cleaning substrates used for cleaning hard surfaces, such as a kitchen, bathroom or other hard surface.

2. Description of the Related Art

When cleaning wipes are impregnated with cleaning compositions containing cationic biocides for disinfection, the cleaning operation typically leaves a residue on glossy surfaces. This may be the case because the saturated wipes leave substantial liquid on the surface. When using a spray cleaner, the residue problems are reduced since the consumer typically wipes off the spray cleaner with a dry paper towel. It is the combination of the cleaning substrate saturated with the cleaning composition that makes it difficult to leave a surface free from filming and streaking.

U.S. Pat. No. 6,936,580 and U.S. Pat. No. 6,716,805 to Sherry et al. discloses alkylpolyglucosides with hydrophilic polymers and propylene glycol propylether on nonwoven substrates. U.S. Pat. No. 4,753,844 to Jones et al. discloses alkylpoly-glucosides, ethanol, and isopropanol on nonwoven substrates. U.S. Pat. No. 5,342,534 to Skrobala et al. discloses alkylpolyglucosides and ethanol on nonwoven substrates. U.S. patent application Ser. No. 2005/0121054, and U.S. Pat. No. 7,082,951 to Barnabas et al. discloses alkylpolyglucosides with citric acid and PHMB.

The present invention surprisingly has found a liquid cleaning composition containing a quaternary biocide that when absorbed onto a nonwoven substrate provides surface disinfection with low residue (low filming and streaking) and low foaming during use. The low foam translates to lower filming and streaking and thus significantly improves consumer acceptability for a disinfecting wipe. While not intending to be bound by theory, the premise for achieving low filming and streaking is to have a cleaning composition that does not bead up (i.e. having no increase in contact angle as the composition dries). The choice of surfactant and solvent significanly affects the properties of the formulation as it dries. Most quat based disinfecting wipes products leave significant residue that is particulary noticeable on smooth glossy surfaces. The inventive formulation provides surface disinfection and cleaning while providing low foaming and low residue (i.e. low filming and streaking), thus eliminating the need of a follow up wiping step. The problems associated with residue left after cleaning with wet substrates of the prior art can be avoided by the low residue compositions of the present invention. It is therefore an object of the present invention to provide an antimicrobial cleaning composition in a cleaning substrate that overcomes the disadvantages and shortcomings associated with prior art examples.

SUMMARY OF THE INVENTION

In accordance with the above objects and those that will be mentioned and will become apparent below, one aspect of the present invention comprises a substrate and a cleaning composition comprising 0.1 to 5.0 weight % of a C8 to C10 alkylpolyglucoside, 0.1 to 1.0 weight % of a quaternary ammonium antimicrobial, and 0.1 to 5.0 weight % of a C2 to C4 alcohol.

In accordance with the above objects and those that will be mentioned and will become apparent below, another aspect of the present invention comprises a substrate and a cleaning composition comprising 0.5 to 4.0 weight % of an alkylpolyglucoside, 0.15 to 0.5 weight % of a quaternary ammonium antimicrobial, 0.6 to 3.0 weight % of a glycol ether having a vapor pressure between 0.1 and 2.0 mm Hg at 20° C.; and 0.5 to 3.0 weight % of a C2 to C4 alcohol.

In accordance with the above objects and those that will be mentioned and will become apparent below, another aspect of the present invention comprises a method for disinfecting a hard surface comprising the steps of wiping the surface to be disinfected with a wet cleaning wipe comprising 0.1 to 5.0 weight % of a C8 to C10 alkylpolyglucoside, 0.1 to 1.0 weight % of a quaternary ammonium antimicrobial, 0.1 to 5.0 weight % of a glycol ether having a vapor pressure between 0.1 and 2.0 mm Hg at 20° C., and 0.1 to 5.0 weight % of a C2 to C4 alcohol, leaving a wet surface, and allowing the surface to dry.

Further features and advantages of the present invention will become apparent to those of ordinary skill in the art in view of the detailed description of preferred embodiments below, when considered together with the attached claims.

DETAILED DESCRIPTION OF THE INVENTION

Before describing the present invention in detail, it is to be understood that this invention is not limited to particularly exemplified systems or process parameters that may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

It must be noted that, as used in this specification and the appended claims, the singular forms "a," "an" and "the" include plural referents unless the content clearly dictates otherwise. Thus, for example, reference to a "surfactant" includes two or more such surfactants.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

The cleaning substrate can be used as a disinfectant, sanitizer, and/or sterilizer. As used herein, the term "disinfect" shall mean the elimination of many or all pathogenic microorganisms on surfaces with the exception of bacterial endospores. As used herein, the term "sanitize" shall mean the reduction of contaminants in the inanimate environment to levels considered safe according to public health ordinance, or that reduces the bacterial population by significant numbers where public health requirements have not been established. An at least 99% reduction in bacterial population within a 24 hour time period is deemed "significant." As used herein, the term "sterilize" shall mean the complete elimination or destruction of all forms of microbial life and which is authorized under the applicable regulatory laws to make legal claims as a "Sterilant" or to have sterilizing properties or qualities.

In the application, effective amounts are generally those amounts listed as the ranges or levels of ingredients in the descriptions, which follow hereto. Unless otherwise stated, amounts listed in percentage ("%'s") are in weight percent (based on 100% active) of the cleaning composition alone, not accounting for the substrate weight. Each of the noted cleaner composition components and substrates is discussed in detail below.

As used herein, the term "substrate" is intended to include any material that is used to clean an article or a surface. Examples of cleaning substrates include, but are not limited to nonwovens, sponges, films and similar materials, which can be attached to a cleaning implement, such as a toilet cleaning device. As used herein, "disposable" is used in its ordinary sense to mean an article that is disposed or discarded after a limited number of usage events, preferably less than 25, more preferably less than about 10, and most preferably less than about 2 entire usage events.

As used herein, "wiping" refers to any shearing action that the substrate undergoes while in contact with a target surface. This includes hand or body motion, substrate-implement motion over a surface, or any perturbation of the substrate via energy sources such as ultrasound, mechanical vibration, electromagnetism, and so forth.

As used herein, the terms "nonwoven" or "nonwoven web" means a web having a structure of individual fibers or threads which are interlaid, but not in an identifiable manner as in a knitted web. Nonwoven webs have been formed from many processes, such as, for example, meltblowing processes, spunbonding processes, and bonded carded web processes.

As used herein, the term "polymer" generally includes, but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the molecule. These configurations include, but are not limited to isotactic, syndiotactic and random symmetries.

The term "sponge", as used herein, is meant to mean an elastic, porous material, including, but not limited to, compressed sponges, cellulosic sponges, reconstituted cellulosic sponges, cellulosic materials, foams from high internal phase emulsions, such as those disclosed in U.S. Pat. No. 6,525,106, polyethylene, poly-propylene, polyvinyl alcohol, polyurethane, polyether, and polyester sponges, foams and nonwoven materials, and mixtures thereof.

The term "cleaning composition", as used herein, is meant to mean and include a cleaning formulation having at least one surfactant.

The term "surfactant", as used herein, is meant to mean and include a substance or compound that reduces surface tension when dissolved in water or water solutions, or that reduces interfacial tension between two liquids, or between a liquid and a solid. The term "surfactant" thus includes anionic, nonionic and/or amphoteric agents.

Alkylpolyglucosides

Suitable non-ionic low residue surfactants are the alkylpolysaccharides that are disclosed in U.S. Pat. No. 5,776,872 to Giret et al.; U.S. Pat. No. 5,883,059 to Furman et al.; U.S. Pat. No. 5,883,062 to Addison et al.; and U.S. Pat. No. 5,906,973 to Ouzounis et al. Suitable alkyl polyglucosides for use herein are also disclosed in U.S. Pat. No. 4,565,647 to Llenado describing alkylpolyglucosides having a hydrophobic group containing from about 6 to about 30 carbon atoms, or from about 10 to about 16 carbon atoms and polysaccharide, e.g., a polyglycoside, hydrophilic group containing from about 1.3 to about 10, or from about 1.3 to about 3, or from about 1.3 to about 2.7 saccharide units. Optionally, there can be a polyalkyleneoxide chain joining the hydrophobic moiety and the polysaccharide moiety. A suitable alkyleneoxide is ethylene oxide. Typical hydrophobic groups include alkyl groups, either saturated or unsaturated, branched or unbranched containing from about 8 to about 18, or from about 10 to about 16, carbon atoms. Suitably, the alkyl group can contain up to about 3 hydroxy groups and/or the polyalkyleneoxide chain can contain up to about 10, or less than about 5, alkyleneoxide moieties. Suitable alkyl poly-saccharides are octyl, nonyldecyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses and/or galactoses. Suitable mixtures include coconut alkyl, di-, tri-, tetra-, and pentaglucosides and tallow alkyl tetra-, penta-, and hexaglucosides.

Suitable alkylpolyglycosides (or alkylpolyglucosides) have the formula:

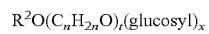

$$R^2O(C_nH_{2n}O)_t(\text{glucosyl})_x$$

wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is about 2 or about 3, preferably about 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4-and/or 6-position, preferably predominantely the 2-position.

A group of alkyl glycoside surfactants suitable for use in the practice of this invention may be represented by formula I below:

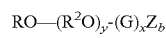

$$RO\text{---}(R^2O)_y\text{-}(G)_xZ_b \qquad I$$

wherein R is a monovalent organic radical containing from about 6 to about 30 (preferably from about 8 to about 18) carbon atoms; $R^2$ is a divalent hydrocarbon radical containing from about 2 to about 4 carbon atoms; 0 is an oxygen atom; y is a number which has an average value from about 0 to about 1 and is preferably 0; G is a moiety derived from a reducing saccharide containing 5 or 6 carbon atoms; and x is a number having an average value from about 1 to 5 (preferably from 1.1 to 2); Z is $O_2M^1$, $O_2CR^3$, $O(CH_2)$, $CO_2M^1$, $OSO_3M^1$, or $O(CH_2)SO_3M^1$; $R^3$ is $(CH_2)CO_2M^1$ or $CH=CHCO_2M^1$; (with the proviso that Z can be $O_2M^1$ only if Z is in place of a primary hydroxyl group in which the primary hydroxyl-bearing carbon atom, —$CH_2OH$, is oxidized to form a —$CO_2M^1$ group); b is a number from 0 to 3x+1 preferably an average of from 0.5 to 2 per glycosal group; p is 1 to 10, $M^1$ is $H^+$ or an organic or inorganic cation, such as, for example, an alkali metal, ammonium, monoethanolamine, or calcium. As defined in Formula I, R is generally the residue of a fatty alcohol having from about 8 to 30 or 8 to 18 carbon atoms. Suitable alkylglycosides include, for example, APG 325® (a $C_9$-$C_{11}$ alkyl polyglycoside available from Cognis Corporation), APG 625® (a $C_{10}$-$C_{16}$ alkyl polyglycoside available from Cognis Corporation), Dow Triton® CG110 (a $C_8$-$C_{10}$ alkyl polyglycoside available from Dow Chemical Company), AG6202® (a $C_8$ alkyl polyglycoside available from Akzo Nobel) and Alkadet 15® (a $C_8$-$C_{10}$ alkyl polyglycoside available from Huntsman Corporation). A C8 to C10 alkylpoly-glucoside includes alkylpolyglucosides wherein the alkyl group is substantially C8 alkyl, substantially C10 alkyl, or a mixture of substantially C8 and C10 alkyl. The C8 to C10 alkylpolyglucoside contains substantially no C9 alkyl or C11 alkyl groups. Suitably, the alkyl polyglycoside is present in the liquid cleaning composition in an amount ranging from about 0.01 to about 5 weight percent, or 0.1 to 5.0 weight percent, or 0.5 to 4 weight percent, or 0.5 to 2.0 weight percent, or 0.1 to 0.5 weight percent.

Additional Surfactants

The cleaning composition may contain one or more additional surfactants selected from anionic, cationic, ampholytic, amphoteric and zwitterionic surfactants and mixtures thereof. A typical listing of anionic, ampholytic, and zwitterionic classes, and species of these surfactants, is given in U.S. Pat. No. 3,929,678 to Laughlin and Heuring. A list of suitable cationic surfactants is given in U.S. Pat. No. 4,259, 217 to Murphy. Where present, anionic, ampholytic, amphotenic and zwitteronic surfactants are generally used in combination with one or more nonionic surfactants. The surfactants may be present at a level of from about 0% to 50%, or from about 0.001% to 10%, or from about 0.1% to 2% by weight, or are absent.

Suitable nonionic surfactants can be found in U.S. Pat. No. 3,929,678 to Laughlin et al. Essentially any alkoxylated nonionic surfactants are suitable herein, for instance, ethoxylated and propoxylated nonionic surfactants. Alkoxylated surfactants can be selected from the classes of the nonionic condensates of alkyl phenols, nonionic ethoxylated alcohols, nonionic ethoxylated/propoxylated fatty alcohols, nonionic ethoxylate/propoxylate condensates with propylene glycol, and the nonionic ethoxylate condensation products with propylene oxide/ ethylene diamine adducts. Suitable anionic surfactants include salts (including, for example, sodium, potassium, ammonium, and substituted ammonium salts such as mono-, di- and tri-ethanolamine salts) of the anionic sulfate, sulfonate, carboxylate and sarcosinate surfactants. Anionic surfactants may comprise a sulfonate or a sulfate surfactant. Anionic surfactants may comprise an alkyl sulfate, a linear or branched alkyl benzene sulfonate, or an alkyldiphenyloxide disulfonate, as described herein. Suitable amphoteric surfactants include the amine oxide surfactants and the alkyl amphocarboxylic acids. Suitable amine oxides include those compounds having the formula $R^3(OR^4)_xNO(R^5)_2$ wherein $R^3$ is selected from an alkyl, hydroxyalkyl, acylamidopropyl and alkylphenyl group, or mixtures thereof, containing from 8 to 26 carbon atoms; $R^4$ is an alkylene or hydroxyalkylene group containing from 2 to 3 carbon atoms, or mixtures thereof, x is from 0 to 5, preferably from 0 to 3; and each $R^5$ is an alkyl or hydroxyalkyl group containing from 1 to 3, or a polyethylene oxide group containing from 1 to 3 ethylene oxide groups. Suitable amine oxides are C10-C 18 alkyl dimethylamine oxide, and C10-18 acylamido alkyl dimethylamine oxide. A suitable example of an alkyl amphodicarboxylic acid is Miranol® C2M Conc. Suitable zwitterionic surfactants include betaines having the formula $R(R^1)_2N^+R^2COO^-$ wherein R is a C6-C18 hydrocarbyl group, each $R^1$ is typically C1-C 3 alkyl, and $R^2$ is a C1-C5 hydrocarbyl group. Suitable betaines are C12-18 dimethyl-ammonio hexanoate and the C10-18 acylamidopropane (or ethane) dimethyl (or diethyl) betaines. Suitable cationic surfactants to be used herein include the quaternary ammonium surfactants. The quaternary ammonium surfactant may be a mono C6-C16, or a C6-C10 N-alkyl or alkenyl ammonium surfactant wherein the remaining N positions are substituted by methyl, hydroxyethyl or hydroxypropyl groups. Suitable are also the mono-alkoxylated and bis-alkoxylated amine surfactants.

Solvents

In one aspect of the invention the composition includes volatile solvents that are substantially soluble in water. In one embodiment, combinations of very volatile solvents and slightly volatile solvents are suitable. While not intended to be bond by theory, the very volatile solvents may volatilize off after application and not form multiple phases that can lead to enhanced filming and streaking. The less volatile solvents may maintain phase stability for the nonvolatile components. The very volatile solvent can have a vapor pressure greater than 10 mm Hg at 20° C. The less volatile solvent can have a vapor pressure greater than 0.1 mm Hg and less than 2.0 mm, or greater than 1.0 mm and less than 2.0 mm at 20° C. The solvents should be greater than 5% soluble, or greater than 25% soluble in water. Examples of solvents are listed in Table A. Suitable very volatile solvents include C2 to C4 alcohols, such as ethanol or isopropanol, and are present in from 0.1% to 5.0%, or from 0.5% to 3.0%, or from 0.1% to 2.0%, or from 0.1% to 3.0%, or from 0.5% to 2.0%, or are absent. Suitable less volatile solvents include propylene glycol ethers and ethylene glycol ethers, such as propylene glycol n-propyl ether, propylene glycol n-butyl ether, propylene glycol t-butyl ether, dipropylene glycol methyl ether, ethylene glycol n-propyl ether, ethylene glycol n-butyl ether, and ethylene glycol n-hexyl ether, and are present in from 0.1% to 5.0%, or from 0.6% to 3.0%., or from 0.1% to 3.0%, or from 0.6% to 5.0%, or from 1.0% to 2.0%, or are absent. The ratio of glycol ethers to alcohols, especially C2 to C4 alcohols, can be less than 2.0, or less than or equal to 1.5, or less than or equal to 1.0.

TABLE A

| Solvent | Vapor pressure Mm Hg (20° C.) | Solubility in water (%) | Surface tension dynes/cm(25° C.) | Specific Heat cal/g K (25° C.) |
|---|---|---|---|---|
| Ethanol | 43 | 100 | 22.3 | 0.618 |
| Isopropanol | 33 | 100 | | 0.65 |
| 1,2-Propylene glycol | 0.07 | 100 | 40.1 | 0.590 |
| Propylene glycol methyl ether | 8.1 | 100 | 27 | 0.58 |
| Propylene | 4.4 | 100 | 29.7 | 0.55 |

TABLE A-continued

| Solvent | Vapor pressure Mm Hg (20° C.) | Solubility in water (%) | Surface tension dynes/cm(25° C.) | Specific Heat cal/g K (25° C.) |
|---|---|---|---|---|
| glycol ethyl ether | | | | |
| Propylene glycol n-propyl ether | 1.8 | 100 | 27.0 | 0.55 |
| Propylene glycol n-butyl ether | 0.62 | 6 | 26.3 | 0.63 |
| Propylene glycol t-butyl ether | 1.9 | 17 | 24.4 | 0.55 |
| Dipropylene glycol methyl ether | 0.17 | 100 | 29.0 | 0.53 |
| Ethylene glycol methyl ether | 6.2 | 100 | 30.8 | 0.53 |
| Ethylene glycol ethyl ether | 3.8 | 100 | 29.3 | 0.56 |
| Ethylene glycol n-propyl ether | 1.3 | 100 | 27.9 | |
| Ethylene glycol n-butyl ether | 0.6 | 100 | 26.6 | 0.56 |
| Diethylene glycol methyl ether | 0.2 | 100 | 34.8 | 0.54 |
| Diethylene glycol ethyl ether | 0.12 | 100 | 32.2 | 0.55 |

Quaternary Ammonium Antimicrobial

A wide range of quaternary compounds can be used as antimicrobial actives. Non-limiting examples of useful quaternary compounds include: (1) benzalkonium chlorides and/or substituted benzalkonium chlorides such as commercially available Barquat® (available from Lonza), Maquat® (available from Mason), Variquat® (available from Witco/Sherex), and Hyamine® (available from Lonza); (2) di(C6-C 14)alkyl di short chain (C1-4 alkyl and/or hydroxyalkl) quaternary such as Bardac® products of Lonza, (3) N-(3-chloroallyl) hexaminium chlorides such as Dowicide® and Dowicil® available from Dow; (4) benzethonium chloride such as Hyamine® from Rohm & Haas; (5) methylbenzethonium chloride represented by Hyamine® 10X supplied by Rohm & Haas, (6) cetylpyridinium chloride such as Cepacol chloride available from of Merrell Labs. Examples of the suitable dialkyl quaternary compounds are di(C8-C12)dialkyl dimethyl ammonium chloride, such as didecyldimethyl-ammonium chloride (Bardac 22), and dioctyldimethylammonium chloride (Bardac 2050). The quaternary compounds useful as cationic antimicrobial actives herein can be selected from the group consisting of dialkyldimethylammonium chlorides, alkyldimethylbenzylammonium chlorides, dialkylmethylbenzylammonium chlorides, and mixtures thereof. Other suitable cationic antimicrobial actives useful herein include diisobutylphenoxyethoxyethyl dimethylbenzylammonium chloride (commercially available under the trade name Hyamine® 1622 from Rohm & Haas) and (methyl) diisobutylphenoxyethoxyethyl dimethylbenzylammonium chloride (i.e. methylbenzethonium chloride).

Other useful cationic antimicrobial actives herein include biguanide compounds, either alone or in combination with other cationic antimicrobial actives. Suitable biguanide compounds include 1,1'-hexamethylene bis(5-(p-chlorophenyl) biguanide), commonly known as chlorhexidine, and its salts, e.g., with hydrochloric, acetic and gluconic acids. Other useful biguanide compounds include Cosmoci® CQ®, Vantocil®IB, including poly(hexamethylene biguanide) hydrochloride. Other useful cationic antimicrobial actives include the bis-biguanide alkanes. Usable water soluble salts of the above are chlorides, bromides, sulfates, alkyl sulfonates such as methyl sulfonate and ethyl sulfonate, phenylsulfonates such as p-methylphenyl sulfonates, nitrates, acetates, gluconates, and the like.

Examples of suitable bis-biguanide compounds are chlorhexidine; 1,6-bis-(2-ethylhexylbiguanidohexane)dihydrochloride; 1,6-di-(N1,N1'-phenyldiguanido-N5, N5')-hexane tetrahydrochloride; 1,6-di-(N1,N1'-phenyl-N1,N1'-methyl-diguanido-N5,N5')-hexane dihydrochloride; 1,6-di(N1,N1'-o-chlorophenyldiguanido-N5,N5')-hexane dihydrochloride; 1,6-di(N1,N1'-2,6-dichlorophenyldiguanido-N5,N5')hexane dihydrochloride; 1,6-di[N1,N1'-β-(p-methoxyphenyl) diguanido-N5,N5']-hexane dihydrochloride; 1,6-di(N1,N1'-α-methyl-β-phenyldiguanido-N5,N5')-hexane dihydrochloride; 1,6-di(N1,N1'-p-nitrophenyldiguanido-N5,N5')hexane dihydrochloride; ω:ω'-di-(N1,N1'-phenyldiguanido-N5, N5')-di-n-propylether dihydrochloride; omega:omega'-di (N1,N1'-p-chlorophenyldiguanido-N5,N5')-di-n-propy-lether tetrahydrochloride; 1,6-di(N1,N1'-2,4-dichlorophenyldiguanido-N5,N5')hexane tetrahydrochloride; 1,6-di(N1,N1'-p-methylphenyl-diguanido-N5,N5')hexane dihydrochloride; 1,6-di(N1,N1'-2,4,5-trichlorophenyldiguanido-N5,N5')hexane tetrahydrochloride; 1,6-di[N1,N1'α-(p-chlorophenyl)ethyldiguanido-N5,N5']hexane dihydrochloride; ω:ω'di(N1,N1'-p-chlorophenyldiguanido-N5,N5')m-xylene dihydrochloride; 1,12-di( N1,N1'-p-chlorophenyldiguanido-N5,N5')dodecane dihydrochloride; 1,10-di(N1,N1'-phenyldiguanido-N5,N5')-decane tetrahydrochloride; 1,12-di(N1,N1'-phenyl-diguanido-N5,N5')dodecane tetrahydrochloride; 1,6-di(N1, N1'-o-chlorophenyl diguanido-N5,N5')hexane dihydrochloride; 1,6-di(N1,N1'-p-chlorophenyldiguanido-N5,N5')-hexane tetrahydrochloride; ethylene bis(1-tolyl biguanide); ethylene bis(p-tolyl biguanide); ethylene bis(3,5-dimethylphenyl biguanide); ethylene bis(p-tert-amylphenyl biguanide); ethylene bis(nonylphenyl biguanide); ethylene bis(phenyl biguanide); ethylene bis(N-butylphenyl biguanide); ethylene bis(2,5-diethoxyphenyl biguanide); ethylene bis(2,4-dimethylphenyl biguanide); ethylene bis(o-diphenylbiguanide); ethylene bis(mixed amyl naphthyl biguanide); N-butyl ethylene bis(phenylbiguanide); trimethylene bis(o-tolyl biguanide); N-butyl trimethylene bis(phenyl biguanide); and the corresponding pharmaceutically acceptable salts of all of the above such as the acetates; gluconates; hydrochlorides; hydrobromides; citrates; bisulfites; fluorides; polymaleates; N-coconutalkylsarcosinates; phosphites; hypophosphites; perfluorooctanoates; silicates; sorbates; salicylates; maleates; tartrates; fumarates; ethylenediaminetetraacetates; iminodiacetates; cinnamates; thiocyanates; arginates; pyromellitates; tetracarboxybutyrates; benzoates; glutarates; monofluorophosphates; and perfluoropropionates, and mixtures thereof.

The quaternary ammonium antimicrobial can be present in from 0.1 to 1% by weight, or from 0.15 to 0.5% by weight, or from 0.1 to 0.5% by weight, or from 0.2 to 1% by weight. In one embodiment, the quaternary ammonium antimicrobial does not contain a biguanide.

Builder/Buffer

The cleaning composition may include a builder or buffer, which increase the effectiveness of the surfactant. The builder or buffer can also function as a softener and/or a sequestering agent in the cleaning composition. A variety of builders or buffers can be used and they include, but are not limited to, phosphate-silicate compounds, zeolites, alkali metal, ammonium and substituted ammonium polyacetates, trialkali salts of nitrilotriacetic acid, carboxylates, polycarboxylates, carbonates, bicarbonates, polyphosphates, aminopolycarboxylates, polyhydroxysulfonates, and starch derivatives.

Builders or buffers can also include polyacetates and polycarboxylates. The polyacetate and polycarboxylate compounds include, but are not limited to, sodium, potassium, lithium, ammonium, and substituted ammonium salts of ethylenediamine tetraacetic acid, ethylenediamine triacetic acid, ethylenediamine tetrapropionic acid, diethylenetriamine pentaacetic acid, nitrilotriacetic acid, oxydisuccinic acid, iminodisuccinic acid, mellitic acid, polyacrylic acid or polymethacrylic acid and copolymers, benzene polycarboxylic acids, gluconic acid, sulfamic acid, oxalic acid, phosphoric acid, phosphonic acid, organic phosphonic acids, acetic acid, and citric acid. These builders or buffers can also exist either partially or totally in the hydrogen ion form.

The builder agent can include sodium and/or potassium salts of EDTA and substituted ammonium salts. The substituted ammonium salts include, but are not limited to, ammonium salts of methylamine, dimethylamine, butylamine, butylenediamine, propylamine, triethylamine, trimethylamine, monoethanolamine, diethanolamine, triethanolamine, isopropanolamine, ethylenediamine tetraacetic acid and propanolamine.

Buffering and pH adjusting agents, when used, include, but are not limited to, organic acids, mineral acids, alkali metal and alkaline earth salts of silicate, metasilicate, polysilicate, borate, hydroxide, carbonate, carbamate, phosphate, polyphosphate, pyrophosphates, triphosphates, tetraphosphates, ammonia, hydroxide, monoethanolamine, monopropanolamine, diethanolamine, dipropanolamine, triethanolamine, and 2-amino-2methylpropanol. Preferred buffering agents for compositions of this invention are nitrogen-containing materials. Some examples are amino acids such as lysine or lower alcohol amines like mono-, di-, and tri-ethanolamine. Other preferred nitrogen-containing buffering agents are tri (hydroxylmethyl) amino methane (TRIS), 2-amino-2-ethyl-1,3-propanediol, 2-amino-2-methylpropanol, 2-amino-2-methyl-1,3-propanol, disodium glutamate, N-methyl diethanolamide, 2-dimethylamino-2-methylpropanol (DMAMP), 1,3-bis(methyl-amine)cyclohexane, 1,3-diamino-propanol N,N'-tetra-methyl-1,3-diamino-2-propanol, N,N-bis(2-hydroxyethyl)glycine (bicine) and N-tris(hydroxymethyl)methyl glycine (tricine). Other suitable buffers include ammonium carbamate, citric acid, acetic acid. Mixtures of any of the above are also acceptable. Useful inorganic buffers/alkalinity sources include ammonia, the alkali metal carbonates and alkali metal phosphates, e.g., sodium carbonate, sodium polyphosphate. For additional buffers see WO 95/07971, which is incorporated herein by reference. Other preferred pH adjusting agents include sodium or potassium hydroxide.

When employed, the builder, buffer, or pH adjusting agent comprises at least about 0.001% and typically about 0.01-5%, or 0.1-1% or 0.1-0.5% by weight of the cleaning composition.

Additional Adjuncts

The cleaning compositions optionally contain one or more of the following adjuncts: stain and soil repellants, lubricants, odor control agents, perfumes, fragrances and fragrance release agents, and bleaching agents. Other adjuncts include, but are not limited to, acids, electrolytes, dyes and/or colorants, solubilizing materials, stabilizers, thickeners, defoamers, hydrotropes, cloud point modifiers, preservatives, and other polymers. The solubilizing materials, when used, include, but are not limited to, hydrotropes (e.g. water soluble salts of low molecular weight organic acids such as the sodium and/or potassium salts of toluene, cumene, and xylene sulfonic acid). The acids, when used, include, but are not limited to, organic hydroxy acids, citric acids, keto acid, and the like. Electrolytes, when used, include, calcium, sodium and potassium chloride. Thickeners, when used, include, but are not limited to, polyacrylic acid, xanthan gum, calcium carbonate, aluminum oxide, alginates, guar gum, clays, methyl, ethyl, and/or propyl hydroxycelluloses. Defoamers, when used, include, but are not limited to, silicones, aminosilicones, silicone blends, and/or silicone/hydrocarbon blends. Bleaching agents, when used, include, but are not limited to, peracids, hypohalite sources, hydrogen peroxide, and/or sources of hydrogen peroxide.

Preservatives, when used, include, but are not limited to, mildewstat or bacteriostat, methyl, ethyl and propyl parabens, short chain organic acids (e.g. acetic, lactic and/or glycolic acids), bisguanidine compounds (e.g. Dantagard® and/or Glydant®) and/or short chain alcohols (e.g. ethanol and/or IPA). The mildewstat or bacteriostat includes, but is not limited to, mildewstats (including non-isothiazolone compounds) include Kathon GC®, a 5-chloro-2-methyl-4-isothiazolin-3-one, KATHON ICP®, a 2-methyl-4-isothiazolin-3-one, and a blend thereof, and KATHON886®, a 5-chloro-2-methyl-4-isothiazolin-3-one, all available from Rohm and Haas Company; BRONOPOL®, a 2-bromo-2-nitropropane 1,3 diol, from Boots Company Ltd., PROXEL CRL®, a propyl-p-hydroxybenzoate, from ICI PLC; NIPA-SOL M®, an o-phenyl-phenol, $Na^+$ salt, from Nipa Laboratories Ltd., DOWICIDE A®, a 1,2-Benzoisothiazolin-3-one, from Dow Chemical Co., and IRGASAN DP 200®, a 2,4,4'-trichloro-2-hydroxydiphenylether, from Ciba-Geigy A.G.

Water

When the composition is an aqueous composition, water can be, along with the solvent, a predominant ingredient. The water can be present at a level of less than 99.9%, or less than about 99%, or less than about 95%. The water can be tap water, soft water, or deionized water. Where the cleaning composition is concentrated, the water may be present in the composition at a concentration of less than about 85 wt.%.

Substrate

The cleaning composition may be part of a cleaning substrate. A wide variety of materials can be used as the cleaning substrate. The substrate should have sufficient wet strength, abrasivity, loft and porosity. Examples of suitable substrates include, nonwoven substrates, wovens substrates, hydroentangled substrates, foams and sponges. Any of these substrates may be water-insoluble, water-dispersible, or water-soluble.

In one embodiment, the cleaning pad of the present invention comprises a nonwoven substrate or web. The substrate is composed of nonwoven fibers or paper. The term nonwoven is to be defined according to the commonly known definition provided by the "Nonwoven Fabrics Handbook" published by the Association of the Nonwoven Fabric Industry. A paper substrate is defined by EDANA (note 1 of ISO 9092-EN29092) as a substrate comprising more than 50% by mass of its fibrous content is made up of fibers (excluding chemically digested vegetable fibers) with a length to diameter ratio of greater than 300, and more preferably also has density of less than 0.040 $g/cm^3$. The definitions of both nonwoven and paper substrates do not include woven fabric or cloth or sponge. The substrate can be partially or fully permeable to water. The substrate can be flexible and the substrate can be resilient, meaning that once applied external pressure has been removed the substrate regains its original shape.

Methods of making nonwovens are well known in the art. Generally, these nonwovens can be made by air-laying, water-laying, meltblowing, coforming, spunbonding, or carding processes in which the fibers or filaments are first cut to desired lengths from long strands, passed into a water or air stream, and then deposited onto a screen through which the fiber- laden air or water is passed. The air-laying process is described in U.S. patent application Ser. No. 2003/0036741 to Abba et al. and U.S. patent application Ser. No. 2003/0118825 to Melius et al. The resulting layer, regardless of its method of production or composition, is then subjected to at least one of several types of bonding operations to anchor the individual fibers together to form a self-sustaining substrate. In the present invention the nonwoven substrate can be prepared by a variety of processes including, but not limited to, air-entanglement, hydroentanglement, thermal bonding, and combinations of these processes.

Additionally, the first layer and the second layer, as well as additional layers, when present, can be bonded to one another in order to maintain the integrity of the article. The layers can be heat spot bonded together or using heat generated by ultrasonic sound waves. The bonding may be arranged such that geometric shapes and patterns, e.g. diamonds, circles, squares, etc. are created on the exterior surfaces of the layers and the resulting article.

The cleaning substrates can be provided dry, pre-moistened, or impregnated with cleaning composition, but dry-to-the-touch. In one aspect, dry cleaning substrates can be provided with dry or substantially dry cleaning or disinfecting agents coated on or in the multicomponent multilobal fiber layer. In addition, the cleaning substrates can be provided in a pre-moistened and/or saturated condition. The wet cleaning substrates can be maintained over time in a sealable container such as, for example, within a bucket with an attachable lid, sealable plastic pouches or bags, canisters, jars, tubs and so forth. Desirably the wet, stacked cleaning substrates are maintained in a resealable container. The use of a resealable container is particularly desirable when using volatile liquid compositions since substantial amounts of liquid can evaporate while using the first substrates thereby leaving the remaining substrates with little or no liquid. Exemplary resealable containers and dispensers include, but are not limited to, those described in U.S. Pat. No. 4,171,047 to Doyle et al., U.S. Pat. No. 4,353,480 to McFadyen, U.S. Pat. No. 4,778,048 to Kaspar et al., U.S. Pat. No. 4,741,944 to Jackson et al., U.S. Pat. No. 5,595,786 to McBride et al.; the entire contents of each of the aforesaid references are incorporated herein by reference. The cleaning substrates can be incorporated or oriented in the container as desired and/or folded as desired in order to improve ease of use or removal as is known in the art. The cleaning substrates of the present invention can be provided in a kit form, wherein a plurality of cleaning substrates and a cleaning tool are provided in a single package.

The substrate can include both natural and synthetic fibers. The substrate can also include water-soluble fibers or water-dispersible fibers, from polymers described herein. The substrate can be composed of suitable unmodified and/or modified naturally occurring fibers including cotton, Esparto grass, bagasse, hemp, flax, silk, wool, wood pulp, chemically modified wood pulp, jute, ethyl cellulose, and/or cellulose acetate. Various pulp fibers can be utilized including, but not limited to, thermomechanical pulp fibers, chemi-thermomechanical pulp fibers, chemi-mechanical pulp fibers, refiner mechanical pulp fibers, stone groundwood pulp fibers, peroxide mechanical pulp fibers and so forth.

Suitable synthetic fibers can comprise fibers of one, or more, of polyvinyl chloride, polyvinyl fluoride, polytetrafluoroethylene, polyvinylidene chloride, polyacrylics such as ORLON®, polyvinyl acetate, Rayon®, polyethylvinyl acetate, non-soluble or soluble polyvinyl alcohol, polyolefins such as polyethylene (e.g., PULPEX®) and polypropylene, polyamides such as nylon, polyesters such as DACRON® or KODELL®, polyurethanes, polystyrenes, and the like, including fibers comprising polymers containing more than one monomer.

The cleaning substrate of this invention may be a multilayer laminate and may be formed by a number of different techniques including but not limited to using adhesive, needle punching, ultrasonic bonding, thermal calendering and through-air bonding. Such a multilayer laminate may be an embodiment wherein some of the layers are spunbond and some meltblown such as a spunbond/meltblown/spunbond (SMS) laminate as disclosed in U.S. Pat. No. 4,041,203 to Brock et al. and U.S. Pat. No. 5,169,706 to Collier, et al., each hereby incorporated by reference. The SMS laminate may be made by sequentially depositing onto a moving conveyor belt or forming wire first a spunbond web layer, then a meltblown web layer and last another spunbond layer and then bonding the laminate in a manner described above. Alternatively, the three web layers may be made individually, collected in rolls and combined in a separate bonding step.

The substrate may also contain superabsorbent materials. A wide variety of high absorbency materials (also known as superabsorbent materials) are known to those skilled in the art. See, for example, U.S. Pat. No. 4,076,663 issued Feb. 28, 1978 to Masuda et al, U.S. Pat. No. 4,286,082 issued Aug. 25, 1981 to Tsubakimoto et al., U.S. Pat. No. 4,062,817 issued Dec. 13, 1977 to Westerman, and U.S. Pat. No. 4,340,706 issued Jul. 20, 1982 to Obayashi et al. The absorbent capacity of such high-absorbency materials is generally many times greater than the absorbent capacity of fibrous materials. For example, a fibrous matrix of wood pulp fluff can absorb about 7-9 grams of a liquid, (such as 0.9 weight percent saline) per gram of wood pulp fluff, while the high-absorbency materials can absorb at least about 15, preferably at least about 20, and often at least about 25 grams of liquid, such as 0.9 weight percent saline, per gram of the high-absorbency material. U.S. Pat. No. 5,601,542, issued to Melius et al., discloses an absorbent article in which superabsorbent material is contained in layers of discrete pouches. Alternately, the superabsorbent material may be within one layer or dispersed throughout the substrate.

Cleaning Implement

In an embodiment of the invention, the cleaning composition may be used with a cleaning implement. In an embodiment of the invention, the cleaning implement comprises the tool assembly disclosed in Co-pending application Ser. No. 10/678033, entitled "Cleaning Tool with Gripping Assembly for a Disposable Scrubbing Head", filed Sep. 30, 2003. In another embodiment of the invention, the cleaning implement comprises the tool assembly disclosed in Co-pending application Ser. No. 10/602478, entitled "Cleaning Tool with Gripping Assembly for a Disposable Scrubbing Head", filed Jun. 23, 2003. In another embodiment of the invention, the cleaning implement comprises the tool assembly disclosed in Co-pending application Ser. No. 10/766179, entitled "Interchangeable Tool Heads", filed Jan. 27, 2004. In another embodiment of the invention, the cleaning implement comprises the tool assembly disclosed in Co-pending application Ser. No. 10/817606, entitled "Ergonomic Cleaning Pad", filed Apr. 1, 2004. In another embodiment of the invention, the cleaning implement comprises the tool assembly disclosed in Co-pending application Ser. No. 10/850213, entitled "Locking, Segmented Cleaning Implement Handle", filed May 19, 2004.

Wipes Dispenser System

Suitable wipes dispenser systems include both individually packaged disinfectant wipes and bulk packaged one or more disinfectant wipes or other suitable disinfecting articles. The dispenser system suitably comprises a sealable container, which is substantially impervious to both liquid and/or gas. The term "container", refers to, but is not limited to, packets containing one or more individual wipes and bulk dispensers, such as canisters, tubs and jars, which dispense one disinfectant wipe at a time, and further feature suitable means to reseal the bulk dispenser between uses to preserve the integrity of the disinfecting articles. One example is a cylindrical canister dispenser that hosts a roll of individual wipes, separated by perforations to permit the tearing off of individual wipes for use. Such dispenser is conveniently gripped by the user and held in position while the user removes a wipe. Suitable dispensers feature a resealable dispensing cap and orifice (See, e.g., Chong, U.S. Pat. No. 6,554,156, of common assignment and incorporated herein by reference thereto) that dispenses individual wipes from a roll and retains the next wipe in a ready-to-dispense position, yet allows sealing of the dispensing cap to close the container against the environment when not in use. A further example, within the scope of the present invention, is to package individual wipes in a non-linked manner, in a dispenser permitting their removal one at a time, as is the case with many wipe/dispenser combinations known in the art.

Wipe dispensers are convenient items that provide moistened sheets or wipes for a variety of uses. Typically, wipes are formulated for specific purposes that include infant wipes, personal care wipes, dishwashing wipes, hard surface treatment wipes, disinfectant wipes, cosmetic or sanitary wipes, hand wipes, wipes used in car cleaning, household or institutional cleaning or maintenance, computer cleaning and maintenance and any other area in which a flexible substrate having a useful liquid treatment composition has application.

Directions for Use

In one embodiment, the directions include wiping the surface clean with the wipe and letting air dry. In one embodiment, the directions include wiping the surface, using enough wipes for the treated surface to remain visibly wet for 30 seconds or 1 minute or 2 minutes or 4 minutes, and letting the surface dry. For highly soiled surfaces, it may be necessary to clean excess dirt first. In one embodiment, the directions include wiping the surface to be disinfected with a wet cleaning wipe and allowing the surface to dry.

EXAMPLES

In Table I, the formulas were loaded onto wipe substrates with a 3.75 loading ratio. The wipe substrates were then wiped on glass mirrors and allowed to dry. Testing was also done on black enamel and ceramic tile surfaces. The examples show the results on mirrors, which were visually examined for filming and streaking and graded from very low filming/streaking to low to medium to high. The C8-C10 alkylpolyglucoside is superior to the amine oxide.

TABLE I

|  | A | B | C | D | E |
|---|---|---|---|---|---|
| Ammonyx LMDO[1] | 0.16 | 0.20 | 0.20 |  |  |
| Alkadet 15 ®[2] |  |  |  | 2.30 | 1.00 |
| PNP[3] |  |  | 1.00 | 2.00 | 1.00 |
| DPNB[4] | 0.59 | 0.60 |  |  |  |
| IPA[5] | 3.60 | 2.00 | 3.00 | 2.00 | 3.00 |
| Barquat 4250Z ®[6] | 0.367 |  | 0.367 | 0.367 | 0.367 |
| Tetrapotassium EDTA |  | 0.06 | 0.06 | 0.06 |  |
| Tripotassium citrate | 0.101 |  |  |  |  |
| Disodium EDTA | 0.101 |  |  |  | 0.10 |
| Monethanolamine |  | 0.30 | 0.30 | 0.30 |  |
| Fragrance | 0.152 | 0.15 | 0.15 | 0.15 | 0.15 |
| Filming/Streaking | High | High | Med | Low | Low |

[1]Amine oxide from Lonza.
[2]C8-10 alkylpolyglucoside from Huntsman.
[3]Propyleneglycol n-propylether.
[4]Dipropyleneglycol n-butyl ether.
[5]Isopropanol.
[6]Quaternary ammonium antimicrobial from Lonza.

In Table II, the levels of PNP and IPA were varied and tested as above.

TABLE II

|  | F | G | H | I | J | K |
|---|---|---|---|---|---|---|
| Alkadet 15 ® | 0.70 | 0.70 | 0.70 | 0.70 | 0.70 | 0.70 |
| PNP | 0.50 | 1.00 | 1.25 | 1.50 | 2.00 | 3.00 |
| IPA | 3.50 | 3.00 | 2.75 | 2.50 | 2.00 | 1.00 |
| Barquat 4250Z ® | 0.367 | 0.367 | 0.367 | 0.367 | 0.367 | 0.367 |
| Tripotassium citrate | 0.100 | 0.100 | 0.100 | 0.100 | 0.100 | 0.100 |
| Disodium EDTA | 0.100 | 0.100 | 0.100 | 0.100 | 0.100 | 0.100 |
| Fragrance | 0.15 | 0.15 | 0.15 | 0.15 | 0.15 | 0.15 |
| Filming/Streaking | High | Med | Low | Low | Low-Med | High |

In Table III, the levels of PNP and IPA were again varied, this time at a 0.80% level of Alkadet 15®, and tested as above.

TABLE III

|  | L | M | N | O | P | Q | R |
|---|---|---|---|---|---|---|---|
| Alkadet 15 ® | 0.80 | 0.80 | 0.80 | 0.80 | 0.80 | 0.80 | 0.80 |
| PNP | 1.00 | 1.00 | 1.00 | 1.00 | 1.00 | 1.00 | 1.00 |
| IPA | 0.50 | 1.00 | 1.50 | 2.00 | 2.50 | 1.25 | 1.70 |
| Barquat 4250Z | 0.367 | 0.367 | 0.367 | 0.367 | 0.367 | 0.367 | 0.367 |
| Tripotassium citrate | 0.100 | 0.100 | 0.100 | 0.100 | 0.100 | 0.100 | 0.100 |
| Disodium EDTA | 0.100 | 0.100 | 0.100 | 0.100 | 0.100 | 0.100 | 0.100 |
| Fragrance | 0.15 | 0.15 | 0.15 | 0.15 | 0.15 | 0.15 | 0.15 |
| Filming/Streaking | Med-High | Med-High | Low | Low | Low | Med | Low |

In Table IV, various glycol ethers were tested as above.

TABLE IV

|  | S | T | U | V | W | Y | Z |
|---|---|---|---|---|---|---|---|
| Alkadet 15 ® | 0.70 |  | 0.70 | 0.70 | 0.70 | 0.70 | 0.70 |
| PNP | 1.00 |  |  |  |  |  |  |
| PNB[7] |  | 1.00 |  |  |  |  |  |
| DPNB |  |  | 1.00 |  |  |  |  |
| DPNP[8] |  |  |  | 1.00 |  |  |  |
| DB[9] |  |  |  |  | 1.00 |  |  |
| EH[10] |  |  |  |  |  | 1.00 |  |
| IPA | 1.70 | 1.70 | 1.70 | 1.70 | 1.70 | 1.70 | 1.70 |
| Barquat 4250Z ® | 0.367 | 0.367 | 0.367 | 0.367 | 0.367 | 0.367 | 0.367 |
| Tripotassium | 0.100 | 0.100 | 0.100 | 0.100 | 0.100 | 0.100 | 0.100 |

TABLE IV-continued

|  | S | T | U | V | W | Y | Z |
|---|---|---|---|---|---|---|---|
| citrate |  |  |  |  |  |  |  |
| Disodium EDTA | 0.100 | 0.100 | 0.100 | 0.100 | 0.100 | 0.100 | 0.100 |
| Fragrance | 0.15 | 0.15 | 0.15 | 0.15 | 0.15 | 0.15 | 0.15 |
| Filming/Streaking | Low | Low | High | High | High | Med | Low |

[7]Propyleneglycol n-butylether
[8]Dipropyleneglycol n-propylether
[9]Diethyleneglycol n-butylether
[10]Ethylenegycol hexylether In Table IV, Alkadet 15® and APG 325®, a C9-C11 alkylpolyglucoside from Cognis, were compared both by the prior procedure on loading on a wipe substrate and also spraying on the tile and wiping dry.

TABLE IV

|  | Spray | Wipe | Spray | Wipe |
|---|---|---|---|---|
| Alkadet 15 ® | 0.70 | 0.70 |  |  |
| APG 325 ® |  |  | 0.70 | 0.70 |
| PNP | 1.00 | 1.00 | 1.00 | 1.00 |
| IPA | 1.70 | 1.70 | 1.70 | 1.70 |
| Barquat 4250Z ® | 0.367 | 0.367 | 0.367 | 0.367 |
| Tripotassium citrate | 0.10 | 0.10 | 0.10 | 0.10 |
| Disodium EDTA | 0.10 | 0.10 | 0.10 | 0.10 |
| Fragrance | 0.15 | 0.15 | 0.15 | 0.15 |
| Filming/Streaking | Low | Low | Low-Med | Med |

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

We claim:

1. A cleaning composition comprising:
    a. 0.1 to 5.0 weight % of a C8 to C10 alkylpolyglucoside wherein the alkyl group is substantially C8 alkyl, substantially C10 alkyl, or a mixture of substantially C8 and C10 alkyl;
    b. 1.0 to 2.0 weight % of a propylene glycol ether or combination of propylene glycol ethers; and
    c. 0.5 to 5% weight % of a C2 to C4 alcohol or combination of C2 to C4 alcohols; and
    d. a quaternary ammonium biocide;
    e. wherein the ratio of the glycol ethers to alcohol is less than 2.0.

2. The cleaning composition of claim 1, wherein the composition comprises 0.1 to 1.0 weight % of the quaternary ammonium antimicrobial.

3. The cleaning composition of claim 1, wherein the composition additionally comprises an alkanolamine selected from the group consisting of monoethanolamine, monopropanolamine, diethanolamine, dipropanolamine, triethanolamine, and combinations thereof.

4. The cleaning composition of claim 1, wherein the ratio of the glycol ethers to alcohol is less than or equal to 1.5.

5. The cleaning composition of claim 1, wherein the ratio of the glycol ethers to alcohol is less than or equal to 1.0.

6. The cleaning composition of claim 1, wherein the glycol ether comprises propylene glycol n-propylether.

7. The cleaning composition of claim 1, wherein the glycol ether comprises propylene glycol n-butylether.

8. The cleaning composition of claim 1, wherein the glycol ether comprises dipropylene glycol methylether.

9. The cleaning composition of claim 1, wherein the glycol ether comprises propylene glycol t-butylether.

10. A cleaning composition comprising:
    a. 0.5 to 4.0 weight % of a C8 to C10 alkylpolyglucoside wherein the alkyl group is substantially C8 alkyl, substantially C10 alkyl, or a mixture of substantially C8 and C10 alkyl;
    b. 0.6 to 3.0 weight % of a propylene glycol ether or combination of propylene glycol ethers; and
    c. 0.5 to 3.0 weight % of a C2 to C4 alcohol.

11. The cleaning composition of claim 10, wherein the composition additionally comprises a quaternary ammonium biocide.

12. The cleaning composition of claim 10, wherein the glycol ether is propylene glycol n-propylether.

13. The cleaning composition of claim 10, wherein the glycol ether is propylene glycol n-butylether.

14. The cleaning composition of claim 10, wherein the glycol ether is dipropylene glycol methylether.

15. The cleaning composition of claim 10, wherein the glycol ether is propylene glycol t-butylether.

16. The cleaning composition of claim 10, wherein the glycol ether is ethylene glycol n-propylether.

17. The cleaning composition of claim 10, wherein the glycol ether is ethylene glycol n-butylether.

18. The cleaning composition of claim 10, wherein the glycol ether is ethylene glycol n-hexylether.

19. The cleaning composition of claim 10, wherein the C8 to C10 alkylpolyglucoside contains substantially no C9 alkyl groups.

20. A cleaning wipe comprising a substrate and a cleaning composition comprising:
    a. 0.1 to 5.0 weight % of a C8 to C10 alkylpolyglucoside wherein the alkyl group is substantially C8 alkyl, substantially C10 alkyl, or a mixture of substantially C8 and C10 alkyl;
    b. 1.0 to 2.0 weight % of a propylene glycol ether or combination of propylene glycol ethers; and
    c. 0.5 to 5% weight % of a C2 to C4 alcohol or combination of C2 to C4 alcohols; and
    d. a quaternary ammonium biocide;
    e. wherein the ratio of the glycol ethers or the alcohol is less than 2.0.

21. The cleaning wipe of claim 19, wherein the glycol ether is selected from the group consisting of propylene glycol n-propylether, propylene glycol n-butylether and combinations thereof.

22. The cleaning wipe of claim 19, wherein the total weight % of the alcohol and the glycol ether is 2.5 weight % or greater.

* * * * *